United States Patent [19]
Miller et al.

[11] Patent Number: 5,671,983
[45] Date of Patent: Sep. 30, 1997

[54] LOCKABLE STORAGE BAG CONTAINING INTERNAL DISPOSED HAND COVERING ELEMENT

[76] Inventors: Angela Miller; Richard L. Miller, both of 12 Parkside Dr., Dix Hills, N.Y. 11746

[21] Appl. No.: 575,077

[22] Filed: Dec. 19, 1995

[51] Int. Cl.$^6$ .................................................. A61G 11/00
[52] U.S. Cl. ........................... 312/1; 312/3; 383/63; 206/438
[58] Field of Search ....................... 312/1, 3, 5, 4, 312/6; 383/63, 41; 206/438, 570

[56] References Cited

U.S. PATENT DOCUMENTS

| | | | |
|---|---|---|---|
| 3,354,922 | 11/1967 | James | 312/1 |
| 3,518,991 | 7/1970 | Goss | 312/3 X |
| 4,335,712 | 6/1982 | Trexler | 312/1 X |
| 4,626,291 | 12/1986 | Natale | 312/1 X |
| 4,883,329 | 11/1989 | Flannery et al. | 312/1 |
| 4,901,743 | 2/1990 | Hittler | 312/1 X |
| 4,911,191 | 3/1990 | Bain | 312/1 X |
| 4,912,358 | 3/1990 | Vitta | 312/1 |
| 5,065,863 | 11/1991 | Moyet-Ortie | 206/438 X |
| 5,147,242 | 9/1992 | Lowe, Jr. | 312/1 X |
| 5,301,806 | 4/1994 | Olson | 206/438 X |
| 5,368,394 | 11/1994 | Scott et al. | 383/63 |
| 5,403,094 | 4/1995 | Tomic | 383/63 |
| 5,489,252 | 2/1996 | May | 383/63 X |
| 5,520,449 | 5/1996 | Klak | 312/1 |
| 5,553,933 | 9/1996 | Ross | 312/1 |

FOREIGN PATENT DOCUMENTS

| | | | |
|---|---|---|---|
| 1146767 | 3/1969 | United Kingdom | 312/1 |
| 8908511 | 9/1989 | WIPO | 312/1 |

*Primary Examiner*—Peter M. Cuomo
*Assistant Examiner*—James O. Hansen
*Attorney, Agent, or Firm*—Richard L. Miller, P.E.

[57] ABSTRACT

An lockable storage bag that includes a receptacle bag, sealing apparatus, and at least one hand covering element. The receptacle bag has a bottom, sides, an open top, and at least one hand covering opening. The securing apparatus opens and closes the open top of the hollow receptacle bag. Each at least one hand covering element is disposed on the receptacle bag at a respective hand covering element. Each hand covering element communicates with the respective hand covering opening and extends inwardly therefrom into the hollow receptacle bag. When a work piece is placed in the receptacle bag and the securing apparatus is closed, the work piece is protected from the environment, and when a hand of a user is placed in the at least one hand covering element, the work piece can be manipulated by the hands of the user without being directly contacted by the hands of the user, simultaneously while the hand or hands of the user are protected from the contents of the receptacle bag.

11 Claims, 2 Drawing Sheets

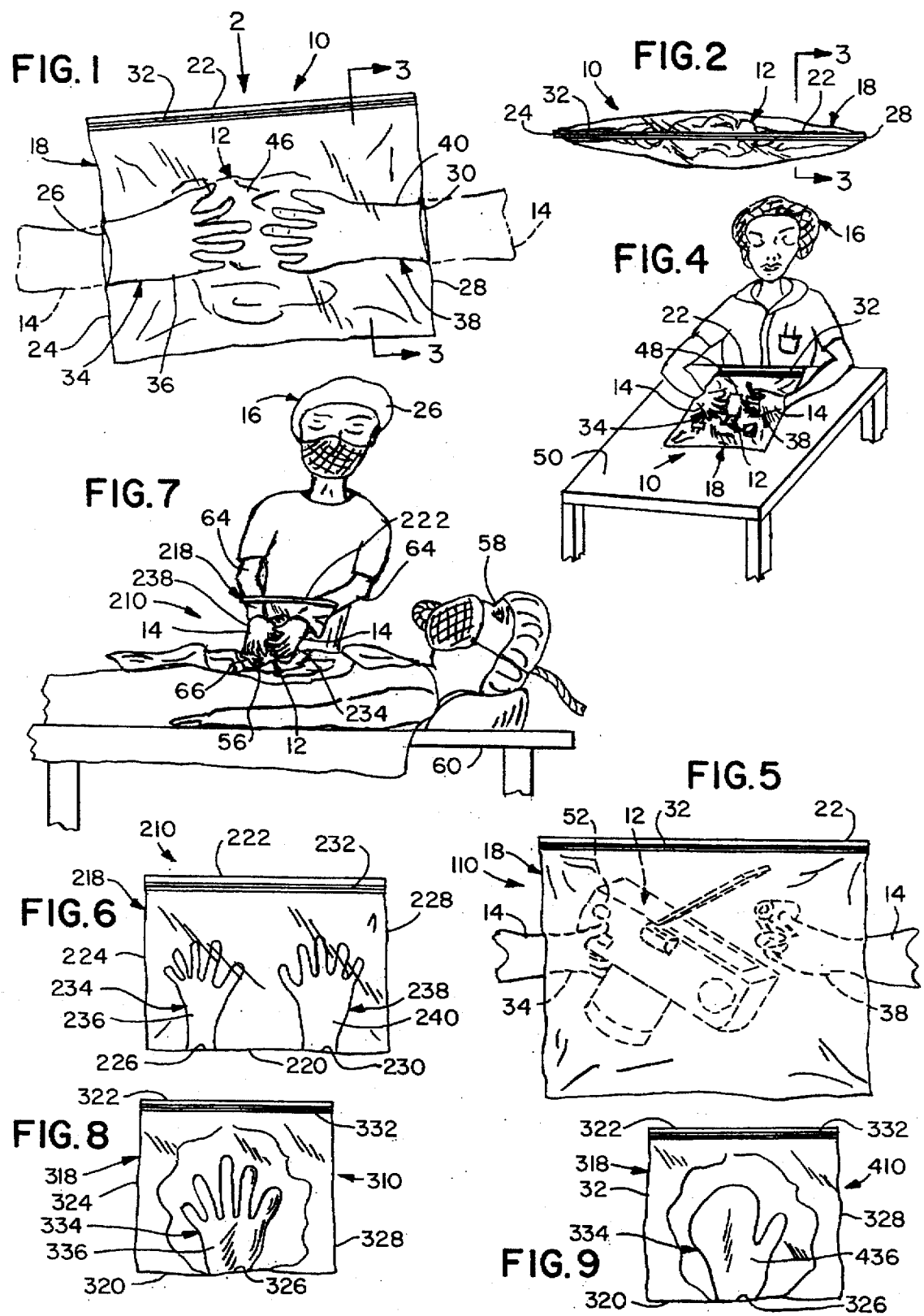

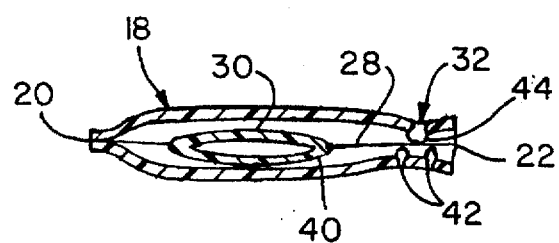
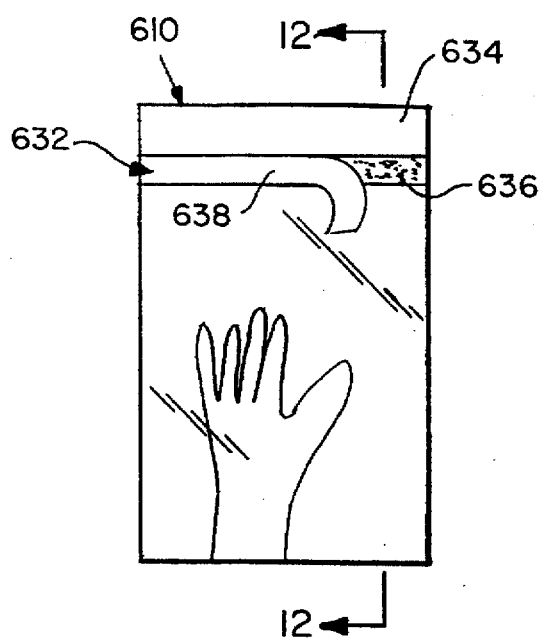
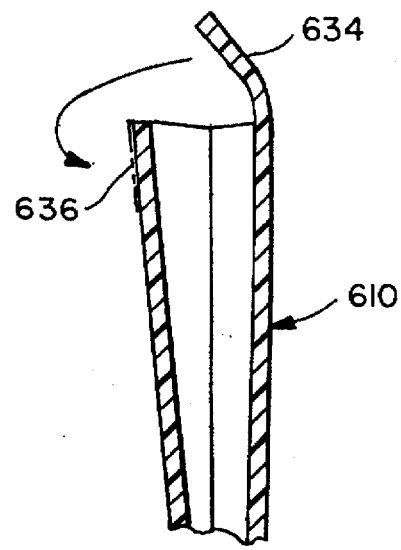
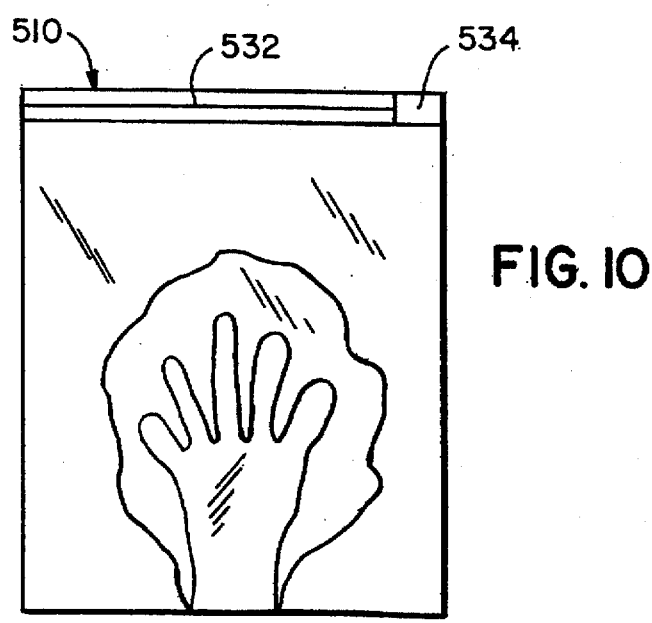

LOCKABLE STORAGE BAG CONTAINING INTERNAL DISPOSED HAND COVERING ELEMENT

BACKGROUND OF THE INVENTION

The present invention relates to a lockable storage bag in the form of a ZIPLOC bag wherein ZIPLOC is a trademark of Dow Brands. More particularly, the present invention relates to a lockable storage bag that contains at least one internally disposed hand covering element that is simultaneously in open communication with the exterior of the lockable storage bag.

A variety of procedures carried out require isolation of a work element on which the procedure is being carried out from the external environment.

FOR EXAMPLE, the kneading of dough and the like must be protected from hair and other contaminants. The kneaders must wear hair nets. Additionally, the kneading of dough causes the flour to become air born and messy.

ANOTHER EXAMPLE, in the assembly of small machinery that requires a clean atmosphere. In such an instance, a clean room is required which restricts the location for assembly.

STILL ANOTHER EXAMPLE, during the surgical removal of a contagious diseased organ that is to be disposed of subsequently, such as one from an AIDS patient.

YET ANOTHER EXAMPLE, during the surgical removal of an organ that is to be analyzed forensically and must be protected from contamination.

STILL YET ANOTHER EXAMPLE, during the capturing of evidence for processing without contamination.

YET STILL ANOTHER EXAMPLE, when a work product requires protection from contamination from and to the user.

STILL YET ANOTHER EXAMPLE, when a camera is to be loaded with film. The loading operation must be accomplished in the dark hindering the vision of the loader.

YET STILL ANOTHER EXAMPLE, when an organ is to be transplanted and must be protected from contaminants.

STILL YET ANOTHER EXAMPLE, when caustic solid pool chemicals that require handling are used and the user's hand is to be protected.

YET STILL ANOTHER EXAMPLE, when a paint brush is temporarily stored and the paint thereon is to be prevented from evaporation.

SUMMARY OF THE INVENTION

ACCORDINGLY, AN OBJECT of the present invention is to provide a lockable storage bag that contains at least one internally disposed hand covering element and avoids the disadvantages of the prior art.

ANOTHER OBJECT of the present invention is to provide a lockable storage bag that contains at least one internally disposed hand covering element that is simple and inexpensive to manufacture.

STILL ANOTHER OBJECT of the present invention is to provide a lockable storage bag that contains at least one internally disposed hand covering element and is simple to use.

YET STILL ANOTHER OBJECT of the present invention is to provide a lockable storage bag that contains at least one internally disposed hand covering element and provides for a variety of procedures to be carried out that require isolation of the work element on which the procedure is being carried out from the external environment.

STILL YET ANOTHER OBJECT of the present invention is to provide a lockable storage bag that contains at least one internally disposed hand covering element and protects dough being kneaded from hair and other external contaminants while preventing the flour from becoming airborne and messy.

YET STILL ANOTHER OBJECT of the present invention is to provide a lockable bag that contains at least one internally disposed hand covering element and provides a clean atmosphere during the assembly of small machinery eliminating the need for a clean room and the restriction of assembly location.

STILL YET ANOTHER OBJECT of the present invention is to provide a lockable storage bag that contains at least one internally disposed hand covering element and allows for the safe surgical removal of an organ that is to be disposed of subsequently, such as one from an AIDS patient.

YET STILL ANOTHER OBJECT of the present invention is to provide a lockable storage bag that contains at least one internally disposed hand covering element and allows for the surgical removal of an organ that is to be analyzed forensically and must be protected from contamination.

STILL YET ANOTHER OBJECT of the present invention is to provide a lockable storage bag that contains at least one internally disposed hand covering element and protects evidence from contamination during capture.

YET STILL ANOTHER OBJECT of the present invention is to provide a lockable storage bag that contains at least one internally disposed hand covering element and eliminates contamination between a work product and a user.

STILL YET ANOTHER OBJECT of the present invention is to provide a lockable storage bag that contains at least one internally disposed hand covering element and allows for loading film into a camera without the need for a dark atmosphere.

YET STILL ANOTHER OBJECT of the present invention is to provide a lockable storage bag that contains at least one internally disposed hand covering element and protects an organ during transplant from contaminants.

STILL YET ANOTHER OBJECT of the present invention is to provide a lockable storage bag that contains at least one internally disposed hand covering element and protects the hand of a user from the effects of caustic solid pool chemicals when handled.

YET STILL ANOTHER OBJECT of the present invention is to provide a lockable storage bag that contains at least one internally disposed hand covering element and prevents paint from evaporating off a brush when the brush is temporarily unused.

BRIEFLY STATED, STILL YET ANOTHER OBJECT of the present invention is to provide a lockable storage bag that includes a hollow receptacle bag, sealing apparatus, a left side hand covering element, and a right side hand covering element.

YET STILL ANOTHER OBJECT of the present invention is to provide a lockable storage bag wherein the hollow receptacle bag has a closed bottom, an open top, a substantially closed left side with an opening, and a substantially closed right side with an opening.

STILL YET ANOTHER OBJECT of the present invention is to provide a lockable storage bag wherein the securing apparatus opens and closes the open top of the hollow receptacle bag.

YET STILL ANOTHER OBJECT of the present invention is to provide a lockable bag wherein the left side hand covering element is disposed on the substantially closed left side of the hollow receptacle bag at the opening of the substantially closed left side of the hollow receptacle bag.

STILL YET ANOTHER OBJECT of the present invention is to provide a lockable storage bag wherein the left side hand covering element communicates with the opening of the substantially closed left side of the hollow receptacle bag and extends inwardly therefrom into the hollow receptacle bag.

YET STILL ANOTHER OBJECT of the present invention is to provide a lockable storage bag wherein the right side hand covering element is disposed on the substantially closed right side of the hollow receptacle bag at the opening of the substantially closed right side of the hollow receptacle bag.

STILL YET ANOTHER OBJECT of the present invention is to provide a lockable storage bag wherein the right side hand covering element communicates with the opening of the substantially closed right side of the hollow receptacle bag and extends inwardly therefrom into the hollow receptacle bag in substantial alignment with the left side hand covering element.

YET STILL ANOTHER OBJECT of the present invention is to provide a lockable storage bag wherein the left side hand covering element is in the form of a glove.

STILL YET ANOTHER OBJECT of the present invention is to provide a lockable storage bag wherein the right side hand covering element is in the form of a glove.

YET STILL ANOTHER OBJECT of the present invention is to provide a lockable storage bag wherein the sealing apparatus includes a pair of spaced apart projections disposed on one side of the open top of the hollow receptacle bag and an opposing projection disposed on an opposing side of the hollow receptacle bag.

STILL YET ANOTHER OBJECT of the present invention is to provide a lockable storage bag wherein the opposing projection is lockingly received intermediate the pair of spaced apart projections.

YET STILL ANOTHER OBJECT of the present invention is to provide a lockable storage bag wherein the sealing apparatus is a slide fastener.

STILL YET ANOTHER OBJECT of the present invention is to provide a lockable storage bag wherein the work piece is selected from a group consisting of dough, small machine parts, and a camera and film.

YET STILL ANOTHER OBJECT of the present invention is to provide a lockable storage bag that includes a hollow receptacle bag, securing apparatus, and at least one hand covering element.

STILL YET ANOTHER OBJECT of the present invention is to provide a lockable storage bag wherein the hollow receptacle bag has a substantially closed bottom with at least one opening, an open top, a closed left side, and a closed right side.

YET STILL ANOTHER OBJECT of the present invention is to provide a lockable storage bag wherein each of the at least one hand covering element is disposed on the substantially closed bottom of the hollow receptacle bag at a respective opening of the substantially closed bottom of the hollow receptacle bag.

STILL YET ANOTHER OBJECT of the present invention is to provide a lockable storage bag wherein each of the at least one hand covering element communicates with the respective opening of the substantially closed bottom of the hollow receptacle bag and extends inwardly therefrom into the hollow receptacle bag.

YET STILL ANOTHER OBJECT of the present invention is to provide a lockable storage bag wherein the at least one hand covering element is two hand covering elements.

STILL YET ANOTHER OBJECT of the present invention is to provide a lockable storage bag wherein one hand covering element is in the form of a glove.

YET STILL ANOTHER OBJECT of the present invention is to provide a lockable storage bag wherein one hand covering element is in the form of a mitten.

STILL YET ANOTHER OBJECT of the present invention is to provide a method of using a lockable storage bag for manipulating a work piece that includes the steps of placing the work piece through the open top of the hollow receptacle bag into the hollow receptacle bag, closing the sealing mechanism so that the work piece is completely contained in the hollow receptacle bag and protected against contaminants, placing a hand of a user in the left side hand covering element, placing another hand of the user in the right side hand covering element, and manipulating the work piece by the hands of the user without being directly contacted by the hands of the user.

YET STILL ANOTHER OBJECT of the present invention is to provide a method of using a lockable storage bag for manipulating a work piece that further includes the steps of opening the sealing mechanism when the manipulating step has been completed and removing the manipulated work piece from the hollow receptacle bag through the open top of the hollow receptacle bag.

STILL YET ANOTHER OBJECT of the present invention is to provide a method of using a lockable storage bag for manipulating a work piece wherein the step of placing a work piece through the open top of the hollow receptacle bag into the hollow receptacle bag includes placing dough through the open top of the hollow receptacle bag into the hollow receptacle bag and the step of manipulating the work piece by the hands of the user without being directly contacted by the hands of the user includes kneading the dough by the hands of the user without being directly contacted by the hands of the user.

YET STILL ANOTHER OBJECT of the present invention is to provide a method of using a lockable storage bag for manipulating a work piece wherein the step of placing a work piece through the open top of the hollow receptacle bag into the hollow receptacle bag includes placing parts of a small machine to be assembled in a clean environment through the open top of the hollow receptacle bag into the hollow receptacle bag and the step of manipulating the work piece by the hands of the user without being directly contacted by the hands of the user includes assembling the parts of the small machine in a clean environment by the hands of the user without being directly contacted by the hands of the user.

STILL YET ANOTHER OBJECT of the present invention is to provide a method of using a lockable storage bag for manipulating a work piece wherein the step of placing a work piece through the open top of the hollow receptacle bag into the hollow receptacle bag includes placing a camera and film through the open top of the hollow receptacle bag that is opaque into the opaque hollow receptacle bag and the step of manipulating the work piece by the hands of the user without being directly contacted by the hands of the user includes loading/unloading the film into the camera by the hands of the user without being directly contacted by the hands of the user and exposed to light.

YET STILL ANOTHER OBJECT of the present invention is to provide a method of using a lockable storage bag for capturing an organ that has been surgically removed that includes the steps of placing a hand of a doctor in the left hand covering element, placing another hand of the doctor in the right hand covering element, inverting the hollow receptacle, pulling the inverted hollow receptacle up and over the arms of the doctor so that the left hand covering element and the right hand covering element are inverted and extend outwardly from the hollow receptacle bag, surgically removing the organ from a patient, grasping the surgically removed organ of the patient in the hands of the doctor, pulling the inverted hollow receptacle bag down and off the arms of the doctor so that the left hand covering element and the right hand covering element again extend inwardly into the hollow receptacle bag, capturing the surgically removed organ of the patient in the hollow receptacle bag, closing the sealing mechanism so that the surgically removed organ of the patient is completely contained in the hollow receptacle bag, and removing the hands of the doctor from the left hand covering element and the right hand covering element and providing for safe handling of the surgically removed organ of the patient.

STILL YET ANOTHER OBJECT of the present invention is to provide a method of using a lockable storage bag as a glove that includes the steps of placing a hand of a user into the hand covering element, inverting the hollow receptacle, and pulling the inverted hollow receptacle up and over the forearm of the user so that the hand covering element is inverted and extends outwardly from the hollow receptacle bag and the hollow receptacle bag covers the forearm of the user and forms a protective barrier.

YET STILL ANOTHER OBJECT of the present invention is to provide a method of using a lockable storage bag as a glove wherein the step of placing a hand of a user into the hand covering element includes placing a hand of a user into a glove-shaped hand covering element.

FINALLY, STILL YET ANOTHER OBJECT of the present invention is to provide a method of using a lockable storage bag as a glove wherein the step of placing a hand of a user into the hand covering element includes placing a hand of a user into a mitten shaped hand covering element.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

THE FIGURES OF THE DRAWING ARE BRIEFLY DESCRIBED AS FOLLOWS:

FIG. 1 is a diagrammatic perspective view of the PREFERRED EMBODIMENT of the instant invention containing dough that is being kneaded and having a pair of internally disposed hand covering elements in the form of gloves disposed on the sides of a lockable storage bag;

FIG. 2 is a diagrammatic top plan view taken in the direction of ARROW 2 in FIG. 1;

FIG. 3 is a cross sectional view taken on LINE 3—3 in FIG. 1 and, FIG. 2;

FIG. 4 is a diagrammatic perspective view of the instant invention containing small parts that are being assembled in a clean environment;

FIG. 5 is a diagrammatic perspective view of the FIRST ALTERNATE EMBODIMENT of the instant invention containing a camera and film being loaded into the camera wherein the bag-like hollow receptacle is opaque;

FIG. 6 is a diagrammatic elevational view of the SECOND ALTERNATE EMBODIMENT of the instant invention containing a pair of internally disposed hand covering elements in the form of gloves disposed on the bottom of the lockable storage bag;

FIG. 7 is a diagrammatic perspective view of the instant invention as embodied in FIG. 6 being used by a surgeon during an operation to remove an organ;

FIG. 8 is a diagrammatic elevational view of the THIRD ALTERNATE EMBODIMENT of the instant invention containing a single internally disposed hand covering element in the form of a glove disposed on the bottom of the lockable storage bag;

FIG. 9 is a diagrammatic elevational view of the FOURTH ALTERNATE EMBODIMENT of the instant invention containing a single internally disposed hand covering element in the form of a mitten disposed on the bottom of the lockable storage bag;

FIG. 10 is a diagrammatic elevational view of the FIFTH ALTERNATE EMBODIMENT of the instant invention wherein the closing mechanism is a slide fastener;

FIG. 11 is a diagrammatic elevational view of the SIXTH ALTERNATE EMBODIMENT of the instant invention wherein the closing mechanism is an adhesive layer with a pull off release strip; and FIG. 12 is a cross sectional view taken on line 12—12 in FIG. 11 with the release strip completely removed and ready for sealing.

LIST OF REFERENCE NUMERALS UTILIZED IN THE DRAWING

Preferred Embodiment 10 lockable storage bag of the present invention
12 work piece
14 hands
16 user
18 hollow bag-shaped receptacle
20 closed bottom
22 openable top
24 substantially closed left side
26 opening
28 substantially closed right side
30 opening
32 sealing mechanism
34 left side hand covering element
36 glove
38 right side hand covering element
40 glove
42 pair of spaced apart projections
44 opposing projection
46 dough
48 small machine
50 table
52 camera
54 film
56 organ
58 patient
60 operating table
62 doctor

First Alternate Embodiment 110 lockable storage bag of the present invention

Second Alternate Embodiment 210 lockable storage bag of the present invention
218 hollow bag-shaped receptacle
220 substantially closed bottom
222 openable top
224 closed left side
226 left opening
228 closed right side
230 right opening
232 sealing mechanism
234 left hand covering element
236 glove
238 right hand covering element
240 glove

Third Alternate Embodiment 310 lockable storage bag of the present invention
318 hollow bag-shaped receptacle
320 substantially closed bottom
322 openable top
324 closed left side
326 single opening
328 closed right side
332 sealing mechanism
334 single hand covering element
336 glove

Fourth Alternate Embodiment 410 lockable storage bag of the present invention
436 mitten

Fifth Alternate Embodiment 510 lockable storage bag of the present invention
532 sealing mechanism
534 slide fastener

Sixth Alternate Embodiment 610 lockable storage bag
632 sealing mechanism
634 flap
636 adhesive layer
638 tear off release strip

DETAILED DESCRIPTION OF THE PREFERRED EMBODIMENT

Referring now to the figures in which like numerals indicate like parts, and particularly to FIGS. 1–5, the lockable storage bag of the present invention is shown generally at 10 containing a work piece 12 being manipulated by hands 14 of a user 16.

The configuration of the PREFERRED EMBODIMENT of the lockable storage bag 10 can best be seen in FIGS. 1–4, and as such, will be discussed with reference thereto.

The lockable storage bag 10 includes a hollow bag-shaped receptacle 18 having a closed bottom 20, an openable top 22, a substantially closed left side 24 with an opening 26, and a substantially closed right side 28 with an opening 30.

A sealing mechanism 32 is disposed on the openable top 22 of the bag-like hollow receptacle 18 and provides for closing and opening of the openable top 22 of the bag-like hollow receptacle 18.

A left side hand covering element 34, in the form of a glove 36, is disposed on the substantially closed left side 24 of the bag-like hollow receptacle 18 at the opening 26 of the substantially closed left side 24 of the bag-like hollow receptacle 18. The left side hand covering element 34 communicates with the opening 26 of the substantially closed left side 24 of the bag-like hollow receptacle 18 and extends inwardly therefrom into the bag-like hollow receptacle 18.

A right side hand covering element 38, in the form of a glove 40, is disposed on the substantially closed right side 28 of the bag-like hollow receptacle 18 at the opening 30 of the substantially closed right side 28 of the bag-like hollow receptacle 18. The right side hand covering element 38 communicates with the opening 30 of the substantially closed right side 28 of the bag-like hollow receptacle 18 and extends inwardly therefrom into the bag-like hollow receptacle 18 in substantial alignment with the left side hand covering element 34.

The configuration of the sealing mechanism 32 can best be seen in FIG. 3, and as such, will be discussed with reference thereto.

The sealing mechanism 32 includes a pair of spaced apart projections 42 and an opposing projection 44 that is receivable intermediate the pair of spaced apart projections 42. Due to the configuration of the pair of spaced apart projections 42 of the sealing mechanism 32 and the opposing projection 44 of the sealing mechanism 32, the opposing projection 44 of the sealing mechanism 32 is received intermediate the pair of spaced apart projections 42 of the sealing mechanism 32 in a locking fashion.

The method of using the PREFERRED EMBODIMENT of the lockable storage bag 10 when the work piece 12 is dough 46 can best be seen in FIGS. 1 and 2, and as such, will be discussed with reference thereto.

The dough 46 is placed through the open top 22 of the bag-like receptacle 18 and the sealing mechanism 32 is closed. The dough 46 is completely contained in the bag-like receptacle 18 and protected against contaminants such as hair.

A hand 14 of a user (not shown) is placed in the left side hand covering element 34 and the other hand 14 of the user (not shown) is placed in the right side hand covering element 38.

The dough 46 can now be kneaded by the hands 14 of the user (not shown) without being directly contacted by the hands 14 of the user (not shown) while the flour raised when the dough 46 is kneaded is contained within the bag-like receptacle 18 and can not become air born and create a mess.

When the kneading of the dough 46 is completed, the sealing mechanism 32 is unsealed and the kneaded dough 46 is removed from the bag-like receptacle 18 through the open top 22 of the bag-like receptacle 18.

The method of using the PREFERRED EMBODIMENT of the lockable storage bag 10 when the work piece 12 is a small machine 48 requiring assembly in a clean environment can best be seen in FIG. 4, and as such, will be discussed with reference thereto.

The small machine 48 requiring assembly is placed through the open top 22 of the bag-like receptacle 18 and the sealing mechanism 32 is closed. The small machine 48 requiring assembly 46 is placed on a work table 50 and is completely contained in the bag-like receptacle 18 and is protected in a clean environment.

A hand 14 of a user 16 is placed in the left side hand covering element 34 and the other hand 14 of the user 16 is placed in the right side hand covering element 38.

The small machine 48 requiring assembly can now be assembled by the hands 14 of the user 16 without being directly contacted by the hands 14 of the user or exposed to the environment.

When the small machine 48 is assembled, the sealing mechanism 32 is opened and the assembled small machine 48 is removed from the bag-like receptacle 18 through the open top 22 of the bag-like receptacle 18.

The configuration of the FIRST ALTERNATE EMBODIMENT of the lockable storage bag 110 can best be seen in FIG. 5, and as such, will be discussed with reference thereto.

The FIRST ALTERNATE EMBODIMENT of the lockable storage bag 110 is identical to the PREFERRED EMBODIMENT of lockable storage bag 10 except that the bag-like hollow receptacle 18 is opaque.

The method of using the FIRST ALTERNATE EMBODIMENT of the lockable storage bag 10 when the work piece 12 is a camera 52 to be loaded with film 54 can best be seen in FIG. 5, and as such, will be discussed with reference thereto.

The camera 52 and the film 54 are placed through the open top 22 of the bag-like receptacle 18 and the sealing mechanism 32 is closed. The camera 52 and the film 54 are completely contained in the bag-like receptacle 18 and protected from light since the bag-like receptacle 18 is opaque.

A hand 14 of a user (not shown) is placed in the left side hand covering element 34 and the other hand 14 of the user (not shown) is placed in the right side hand covering element 38.

The film 54 is now loaded into the camera 52 without being directly contacted by the hands 14 of the user or exposed to light.

When the camera 52 is loaded with the film 54, the sealing mechanism 32 is opened and the loaded camera 52 is removed from the bag-like receptacle 18 through the open top 22 of the bag-like receptacle 18.

The configuration of the SECOND ALTERNATE EMBODIMENT of the lockable storage bag 210 can best be seen in FIG. 6, and as such, will be discussed with reference thereto.

The SECOND ALTERNATE EMBODIMENT of the lockable storage bag 210 includes a hollow bag-shaped receptacle 218 having a substantially closed bottom 220 with a left opening 226 and a right opening 230, a closed left side 224, an openable top 222, a closed right side 228, and a sealing mechanism 232.

The configuration and positioning of the sealing mechanism 232 is identical to that of the sealing mechanism 32 making a detailed discussion unnecessary.

A left hand covering element 234, in the form of a glove 236, is disposed on the substantially closed bottom 220 of the bag-like hollow receptacle 218 at the left opening 226 of the substantially closed bottom 220 of the bag-like hollow receptacle 218. The left hand covering element 234 communicates with the opening 226 of the substantially closed bottom 220 of the bag-like hollow receptacle 218 and extends inwardly therefrom into the bag-like hollow receptacle 218.

A right hand covering element 238, in the form of a glove 240, is disposed on the substantially closed bottom 220 of the bag-like hollow receptacle 218 at the right opening 230 of the substantially closed bottom 220 of the bag-like hollow receptacle 218. The right hand covering element 238 communicates with the right opening 230 of the substantially closed bottom 220 of the bag-like hollow receptacle 218 and extends inwardly therefrom into the bag-like hollow receptacle 218.

The method of using the SECOND ALTERNATE EMBODIMENT of the lockable storage bag 210 when the work piece 12 is an organ 56 being surgically removed from a patient 58 lying on an operating table 60 by the user 16 who is a doctor 62 can best be seen in FIG. 7, and as such, will be discussed with reference thereto.

The hand 14 of the doctor 62 is placed in the left hand covering element 234 and the other hand 14 of the doctor 62 is placed in the right hand covering element 238. The bag-like hollow receptacle 218 in then inverted and pulled up and over the arms 64 of the doctor 62 so that the left hand covering element 234 and the right hand covering element 238 are inverted and extend outwardly from the bag-like hollow receptacle 218.

The doctor 62 then proceeds to surgically remove the organ 56 from the patient 58. After the organ 56 has been severed from the body 66 of the patient 58 it is grasped in the hands 14 of the doctor 62. The bag-like hollow receptacle 218 in then pulled down and off the arms 64 of the doctor 62 so that the left hand covering element 234 and the right hand covering element 238 again extend inward in the bag-like hollow receptacle 218 capturing the organ 56 in the bag-like hollow receptacle 218.

At this point, the sealing mechanism 32 is closed and the organ 56 is completely contained in the bag-like receptacle 218. The hands 14 of the doctor 62 are removed from the left hand covering element 234 and the right hand covering element 238 providing for safe handling of the organ 56.

The configuration of the THIRD ALTERNATE EMBODIMENT of the lockable storage bag 310 can best be seen in FIG. 8, and as such will be discussed with reference thereto.

The THIRD ALTERNATE EMBODIMENT of the lockable storage bag 310 includes a hollow bag-shaped receptacle 318 having a substantially closed bottom 320 with a single opening 326, a closed left side 324, an openable top 322, a closed right side 328, and a sealing mechanism 332.

The configuration and positioning of the sealing mechanism 332 is identical to that of the sealing mechanisms 32 and 232 making a detailed discussion unnecessary.

A single hand covering element 334, in the form of a glove 336, is disposed on the substantially closed bottom 320 of the bag-like hollow receptacle 318 at the opening 326 of the substantially closed bottom 320 of the bag-like hollow receptacle 318. The single hand covering element 334 communicates with the opening 326 of the substantially closed bottom 320 of the bag-like hollow receptacle 318 and extends inwardly therefrom into the bag-like hollow receptacle 318.

The method of using the THIRD ALTERNATE EMBODIMENT of the lockable storage bag 310 as a glove can best be seen in FIG. 8, and as such, will be discussed with reference thereto.

A hand (not shown) of a user (not shown) is placed in the single hand covering element 334. The bag-like hollow receptacle 318 in then inverted and pulled up and over the forearm (not shown) of the user (not shown). The single hand covering element 334 is now inverted and extends outwardly from the bag-like hollow receptacle 318. The inverted bag-like hollow receptacle covers the forearm (not shown) of the user (not shown) and forms a protective barrier.

The configuration and method of using the FOURTH ALTERNATE EMBODIMENT of the lockable storage bag 410 can best be seen in FIG. 9, and as such, will be discussed with reference thereto.

The FOURTH ALTERNATE EMBODIMENT of the lockable storage bag 410 is identical to the THIRD ALTERNATE EMBODIMENT of the lockable storage bag 310 except that the single hand covering element 334 is a mitten 436.

The configuration of the FIFTH ALTERNATE EMBODIMENT of the lockable storage bag 510 can best be seen in FIG. 10, and as such, will be discussed with reference thereto.

The FIFTH ALTERNATE EMBODIMENT of the lockable storage bag 510 includes a sealing mechanism 532 that is a slide fastener 534 sold under the name ONEZIP which is a trademark of the Mobil Chemical Company.

The configuration of the SIXTH ALTERNATE EMBODIMENT of the lockable storage bag 610 can best be seen in FIGS. 11 and 12, and as such, will be discussed with reference thereto.

The SIXTH ALTERNATE EMBODIMENT of the lockable storage bag 610 includes a sealing mechanism 632 that has a foldable flap 634 engagable with an adhesive layer 636 that is protected by a tear off release strip 638.

The SIXTH ALTERNATE EMBODIMENT of the lockable storage bag 610 is particularly suited for surgical procedures where the contents of the lockable storage bag 610 are to be permanently discarded.

It will be understood that each of the elements described above, or two or more together, may also find a useful application in other types of constructions differing from the types described above.

While the invention has been illustrated and described as embodied in a lockable storage bag containing at least one internally disposed hand covering element, it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. A lockable storage bag, comprising:
   a) a hollow receptacle bag having a closed bottom edge, an open top edge, a substantially closed left edge with an opening therein, and a substantially closed right edge with an opening therein and being substantially parallel to said substantially closed left edge of said hollow receptacle bag;
   b) securing means for opening and closing said open top edge of said hollow receptacle bag;
   c) a left side hand covering element disposed on said substantially closed left edge of said hollow receptacle bag, at said opening in said substantially closed left edge of said hollow receptacle bag; said left side hand covering element communicating with said opening in said substantially closed left edge of said hollow receptacle bag and extending inwardly therefrom into said hollow receptacle bag; and
   d) a right side hand covering element disposed on said substantially closed right edge of said hollow receptacle bag, at said opening in said substantially closed right edge of said hollow receptacle bag; said right side hand covering element communicating with said opening in said substantially closed right edge of said hollow receptacle bag and extending inwardly therefrom into said hollow receptacle bag; said right hand covering element opposing, and being in substantial longitudinal alignment with, said left side hand covering element by virtue of said substantially closed right edge of said hollow receptacle bag being substantially parallel to said substantially closed left edge of said hollow receptacle bag and said left hand covering element extending inwardly from said substantially closed left edge of said hollow receptacle bag and said right hand covering element extending inwardly from said substantially closed right edge of said hollow receptacle bag.

2. The bag as defined in claim 1, wherein said left side hand covering element is in the form of a glove.

3. The bag as defined in claim 1, wherein said right side hand covering element is in the form of a glove.

4. The bag as defined in claim 1, wherein said sealing means includes a pair of spaced apart projections disposed on one side of said open top edge of said hollow receptacle bag and an opposing projection disposed on an opposing side of said hollow receptacle bag; said opposing projection is lockingly received intermediate said pair of spaced apart projections.

5. The bag as defined in claim 1, wherein said sealing means is a slide fastener.

6. A lockable storage bag, comprising:
   a) a hollow receptacle bag having a substantially closed bottom edge with only one opening therein, an open top edge, a closed left edge, and a closed right edge;
   b) securing means for opening and closing said open top edge of said hollow receptacle bag; and
   c) only one hand covering element disposed on said substantially closed bottom edge of said hollow receptacle bag, at said only one opening in said substantially closed bottom edge of said hollow receptacle bag; said hand covering element communicating with said only one opening in said substantially closed bottom edge of said hollow receptacle bag and extending inwardly therefrom into said hollow receptacle bag.

7. The bag as defined in claim 6, wherein said only one hand covering element is in the form of a glove.

8. The bag as defined in claim 6, wherein said only one hand covering element is in the form of a mitten.

9. The bag as defined in claim 6, wherein said sealing means includes a pair of spaced apart projections disposed on one side of said open top edge of said hollow receptacle bag and an opposing projection disposed on an opposing side of said hollow receptacle bag; said opposing projection is lockingly received intermediate said pair of spaced apart projections.

10. The bag as defined in claim 6, wherein said sealing means is a slide fastener.

11. The bag as defined in claim 6, wherein said sealing means is a foldable flap engagable with an adhesive layer that is protected by a tear off release strip.

* * * * *